(12) United States Patent
Dalal

(10) Patent No.: US 7,174,216 B1
(45) Date of Patent: *Feb. 6, 2007

(54) NOTIFICATION SYSTEM FOR IMPLANTABLE CARDIAC THERAPY DEVICES

(75) Inventor: Nirav Dalal, North Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 461 days.

This patent is subject to a terminal disclaimer.

(21) Appl. No.: 10/652,982

(22) Filed: Aug. 28, 2003

Related U.S. Application Data

(63) Continuation-in-part of application No. 10/008,592, filed on Nov. 9, 2001, now Pat. No. 6,842,645.

(51) Int. Cl.
*A61N 1/00* (2006.01)

(52) U.S. Cl. .......................................... 607/60

(58) Field of Classification Search .............. 607/5, 607/27–30, 46, 60; 128/899
See application file for complete search history.

(56) References Cited

U.S. PATENT DOCUMENTS

| | | | |
|---|---|---|---|
| 5,113,869 A | 5/1992 | Nappholz et al. | |
| 5,342,408 A | 8/1994 | deCoriolis et al. | |
| 5,454,838 A | 10/1995 | Vallana et al. | |
| 5,496,351 A | 3/1996 | Plicchi et al. | |
| 5,511,553 A | 4/1996 | Segalowitz | |
| 5,518,001 A | 5/1996 | Snell | |
| 5,544,661 A | 8/1996 | Davis et al. | |
| 5,562,713 A | 10/1996 | Silvian | |
| 5,720,770 A | 2/1998 | Nappholz et al. | |
| 5,752,976 A | 5/1998 | Duffin et al. | |
| 5,824,021 A * | 10/1998 | Rise | 607/46 |
| 5,836,975 A * | 11/1998 | DeGroot | 607/5 |
| 5,904,708 A | 5/1999 | Goedeke | |
| 6,004,276 A | 12/1999 | Wright et al. | |
| 6,083,248 A | 7/2000 | Thompson | |
| 6,104,392 A | 8/2000 | Shaw et al. | 345/335 |
| 6,155,267 A | 12/2000 | Nelson | |
| 6,162,180 A | 12/2000 | Miesel et al. | |
| 6,200,265 B1 | 3/2001 | Walsh et al. | |
| 6,225,901 B1 | 5/2001 | Kail, IV | |
| 6,238,492 B1 | 5/2001 | Nakanishi et al. | |
| 6,250,309 B1 | 6/2001 | Krichen et al. | 128/899 |
| 6,264,614 B1 | 7/2001 | Albert et al. | |
| 6,270,457 B1 | 8/2001 | Bardy | |
| 6,282,441 B1 | 8/2001 | Raymond et al. | |
| 6,301,504 B1 | 10/2001 | Silvian | |
| 6,312,378 B1 | 11/2001 | Bardy | |
| 6,315,721 B2 | 11/2001 | Schulman et al. | |
| 6,354,299 B1 * | 3/2002 | Fischell et al. | 128/899 |
| 6,564,104 B2 | 5/2003 | Nelson et al. | 607/60 |

* cited by examiner

*Primary Examiner*—George Manuel

(57) ABSTRACT

An implementation of a technology, described herein, for implantable medical therapy devices and techniques related to notifications related to the use of such devices. One implementation, described herein, provides a notification system for notifying implantable cardiac therapy device (ICTD) patients (and possibly others) in a manner that is comprehensive, integrated, efficient, effective, and quick. This abstract itself is not intended to limit the scope of this patent. The scope of the present invention is pointed out in the appending claims.

9 Claims, 10 Drawing Sheets

NOTIFICATION SYSTEM FOR IMPLANTABLE CARDIAC THERAPY DEVICES

INCORPORATION BY REFERENCE

This application is a continuation-in-part of copending U.S. patent application Ser. No. 10/008,592 titled "Presentation Architecture for Network Supporting Implantable Cardiac Therapy Devices" filed on Nov. 9, 2001 now U.S. Pat. No. 6,842,645.

The following copending patent applications, which are all assigned to the same assignee as the present application, are incorporated by reference herein:

- U.S. patent application Ser. No. 10/652,975, titled "Data Communications Architecture Including Implantable Cardiac Therapy Devices," filed concurrently herewith;
- U.S. patent application Ser. No. 10/002,798, titled "Magnetic Coupling Antennas for Implantable Medical Devices," filed Nov. 1, 2001;
- U.S. patent application Ser. No. 10/001,225, titled "Frequency Agile Telemetry System for Implantable Medical Device," filed Nov. 2, 2001;
- U.S. patent application Ser. No. 10/039,743, titled "Implantable Cardiac Therapy Device with Dual Chamber Can to Isolate High-Frequency Circuitry," filed Oct. 26, 2001; and
- U.S. patent application Ser. No. 10/638,065, titled "Data Feedback Loop for Medical Therapy Adjustment," filed Aug. 8, 2003.

TECHNICAL FIELD

This invention generally concerns implantable medical therapy devices and techniques related to notifications related to the use of such devices.

BACKGROUND

Implantable cardiac therapy devices (ICTDs) are implanted within the body of a patient to monitor, regulate, and/or correct heart function. ICTDs include implantable cardiac stimulation devices (e.g., implantable cardiac pacemakers, implantable defibrillators) that apply stimulation therapy to the heart as well as implantable cardiac monitors that monitor heart activity.

ICTDs typically include a control unit positioned within a casing that is implanted into the body and a set of leads that are positioned to impart stimulation and/or monitor cardiac activity. With improved processor and memory technologies, the control units have become increasingly more sophisticated, allowing them to monitor many types of conditions and apply tailored stimulation therapies in response to those conditions.

ICTDs are typically capable of being programmed remotely by an external programming device, often called a "programmer". Today, individual ICTDs are equipped with telemetry circuits that communicate with the programmer. One type of programmer utilizes an electromagnetic wand that is placed near the implanted cardiac device to communicate with the implanted device. When used in a sterile field, the wand may be enclosed in a sterile sheath. The wand contains a coil that forms a transformer coupling with the ICTD telemetry circuitry. The wand transmits low frequency signals by varying coil impedance.

Early telemetry systems were passive, meaning that the communication was unidirectional from the programmer to the implanted device. Passive telemetry allowed a treating physician to download instructions to the implanted device following implantation. Due to power and size constraints, early commercial versions of the implanted devices were incapable of transmitting information back to the programmer.

As power capabilities improved, active telemetry became feasible, allowing synchronous bi-directional communication between the implanted device and the programmer. Active telemetry utilizes a half-duplex communication mode in which the programmer sends instructions in a predefined frame format and, following termination of this transmission, the implanted device returns data using the frame format. With active telemetry, the treating physician is able to not only program the implanted device, but also retrieve information from the implanted device to evaluate heart activity and device performance. The treating physician may periodically want to review device performance or heart activity data for predefined periods of time to ensure that the device is providing therapy in desired manner. Consequently, current generation implantable cardiac therapy devices incorporate memories, and the processors periodically sample and record various performance parameter measurements in the memories.

Data pertaining to a patient's cardiac condition is gathered and stored by the programmer during programming sessions of the ICTDs. Analysis of the cardiac condition is performed locally by the programming software. Programmers offer comprehensive diagnostic capabilities, high-speed processing, and easy operation, thereby facilitating efficient programming and timely patient follow-up.

In addition to local analysis, TransTelephonic Monitoring (TTM) systems are employed to gather current cardiac data from patients who are remote from the healthcare provider. TTM systems are placed in patients' homes. They typically include a base unit that gathers information from the ICTD much like the programmer would. The base unit is connected to a telephone line so that data may be transmitted to the medical staff responsible for that patient. An example of an ICTD TTM system is a service from St. Jude Medical® and Raytel® Cardiac Services called "Housecall™." This service provides current programmed parameters and episode diagnostic information for a plurality of events including stored electrograms (EGMs). Real-time EGMs with annotated status information can also be transmitted.

Using a telephone and a transmitter, the TTM system provides both the medical staff and the patient the convenience of instant analysis of therapy without having the patient leave the comfort of home. Typically, real-time measurements are transmitted in just minutes. Patients may be closely monitored, and the medical staff has more control of their patient's treatment, thus administering better patient management.

One challenge that still persists, however, is how to efficiently, effectively, and quickly notify a patient. Based on numerous factors, it may be advisable to notify the patient quickly. However, there is no existing comprehensive, integrated, efficient, effective, and quick mechanism for doing so. Furthermore, there is no existing system for notifying those who are not ICTD patients about information related to their use.

SUMMARY

Described herein is a technology for implantable medical therapy devices and techniques related to notifications related to the use of such devices. One implementation, described herein, provides a notification system for notifying implantable cardiac therapy device (ICTD) patients (and possibly others) in a manner that is comprehensive, integrated, efficient, effective, and quick.

This summary itself is not intended to limit the scope of this patent. Moreover, the title of this patent is not intended to limit the scope of this patent. For a better understanding of the present invention, please see the following detailed description and appending claims, taken in conjunction with the accompanying drawings. The scope of the present invention is pointed out in the appending claims.

BRIEF DESCRIPTION OF THE DRAWINGS

Generally, the same numbers are used throughout the drawings to reference like elements and features. Further features and advantages of the claimed embodiments can be more readily understood by reference to the following description taken in conjunction with the accompanying drawings.

DETAILED DESCRIPTION

In the following description, for purposes of the explanation, specific numbers, materials and configurations are set forth in order to provide a thorough understanding of the present invention. However, it will be apparent to one skilled in the art that the present invention may be practiced without the specific exemplary details. In other instances, well-known features are omitted or simplified to clarify the description of the exemplary implementations of present invention, thereby better explain the present invention. Furthermore, for ease of understanding, certain method steps are delineated as separate steps; however, these separately delineated steps should not be construed as necessarily order dependent in their performance.

The following description sets forth one or more exemplary implementations of present invention that incorporate elements recited in the appended claims. These implementations are described with specificity in order to meet statutory written description, enablement, and best-mode requirements. However, the description itself is not intended to limit the scope of this patent.

The inventors intend these exemplary implementations to be examples. The inventors do not intend these exemplary implementations to limit the scope of the present invention. Rather, the inventors have contemplated that the present invention might also be embodied and implemented in other ways, in conjunction with other present or future technologies.

An example of an embodiment of a may be referred to as an "exemplary notification system."

Overview

Figure 1:
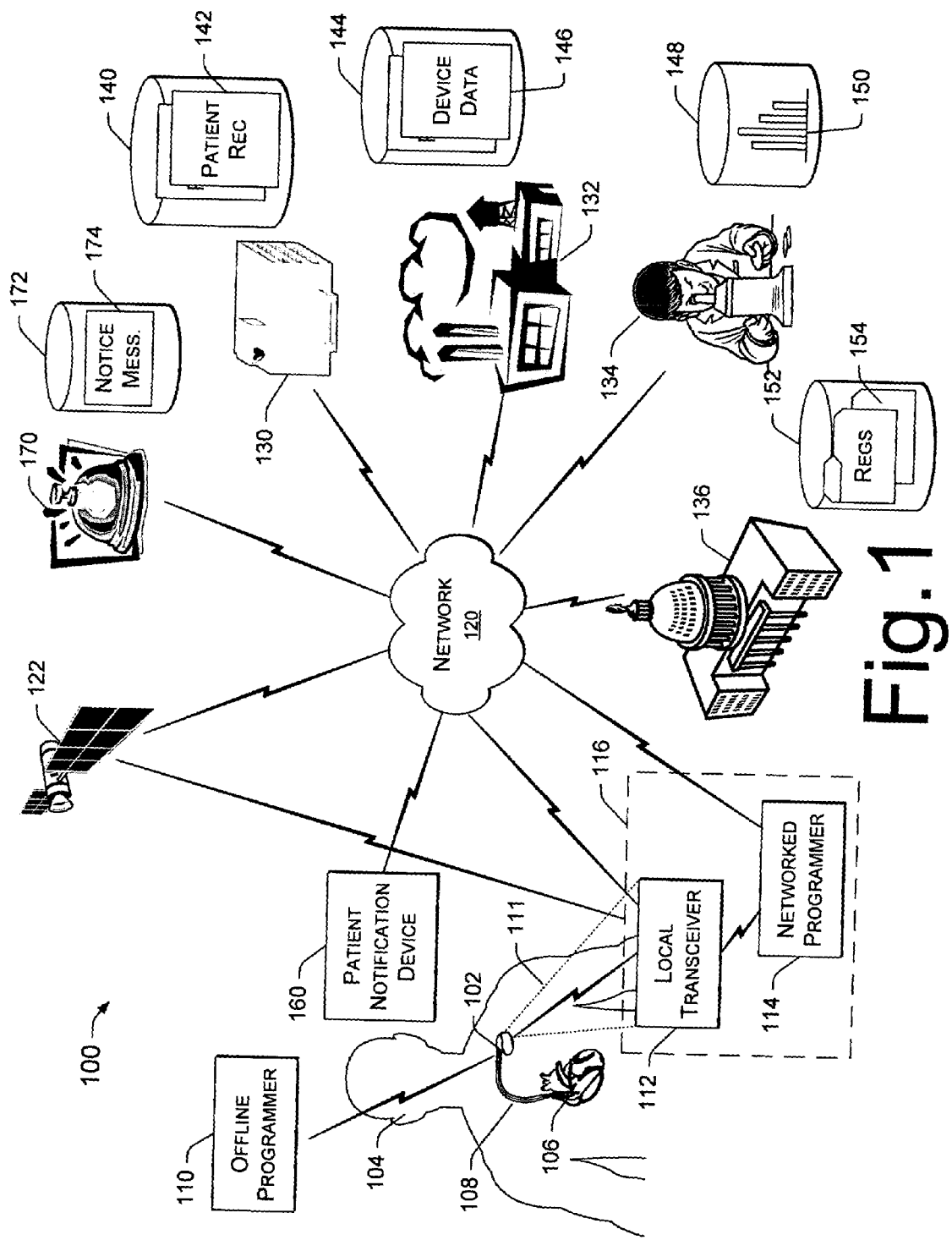
FIG. 1 is a diagrammatic illustration of a cardiac therapy network architecture with an implantable cardiac therapy device (ICTD) connected to a network of computing systems used by various knowledge workers.

The one or more exemplary implementations, described herein, of the present invention may be implemented (in whole or in part) by an exemplary cardiac therapy network architecture 100 like that shown in FIG. 1.

With at least one embodiment, the exemplary notification system may send information and notifications to a user of an implantable cardiac therapy device (ICTD). This user may be called an ICTD patient. Such notifications may be sent manually from a knowledge worker to the patient. Alternatively, such notifications may be automatically generated based upon one or more triggering events or determinations.

Furthermore, the exemplary notification system may send notifications to those who are not ICTD patients about the use of the device. For example, it may send device-related information (e.g., raw IEGM data) for notification to the patient's physician or alternatively to manufacturer of the device.

Cardiac Therapy Network

FIG. 1 shows an exemplary cardiac therapy network architecture 100 that includes an implantable cardiac therapy device (ICTD) 102 coupled to a network of computing systems associated with various knowledge workers who have interest in cardiac therapy. The ICTD is illustrated as being implanted in a human patient 104. The ICTD 102 is in electrical communication with a patient's heart 106 by way of multiple leads 108 suitable for monitoring cardiac activity and/or delivering multi-chamber stimulation and shock therapy.

The ICTD 102 may communicate with a standalone or offline programmer 110 via short-range telemetry technology. The offline programmer 110 is equipped with a wand that, when positioned proximal to the ICTD 102, communicates with the ICTD 102 through a magnetic coupling.

The ICTD 102 can alternatively, or additionally, communicate with a local transceiver 112. The local transceiver 112 may be a device that resides on or near the patient, such as an electronic communications device that is worn by the patient or is situated on a structure within the room or residence of the patient. The local transceiver 112 communicates with the ICTD 102 using short-range telemetry or longer-range high-frequency-based telemetry, such as RF (radio frequency) transmissions. Alternatively, the local transceiver 112 may be incorporated into the ICTD 102, as represented by dashed line 111. In this case, the ICTD includes a separate and isolated package area that accommodates high-frequency transmissions without disrupting operation of the monitoring and stimulation circuitry.

Depending upon the implementation and transmission range, the local transceiver 112 can be in communication with various other devices of the network architecture 100. One possible implementation is for the local transceiver 112 to transmit information received from the ICTD 102 to a networked programmer 114, which is connected to network 120. The networked programmer 114 is similar in operation to standalone programmer 110, but differs in that it is connected to the network 120. The networked programmer 114 may be local to, or remote from, the local transceiver 112; or alternatively, the local transceiver 112 may be incorporated into the networked programmer 114, as represented by dashed line 116.

Another possible implementation is for the local transceiver to be connected directly to the network 120 for communication with remote computing devices and/or programmers. Still another possibility is for the local transceiver 112 to communicate with the network 120 via wireless communication, such as via a satellite system 122.

The network 120 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 120 can be configured to support any number of different protocols, including HTTP (HyperText Transport Protocol), TCP/IP (Transmission Control Protocol/Internet Protocol), WAP (Wireless Application Protocol), Bluetooth, and so on.

A number of knowledge workers are interested in data gathered from the implantable cardiac therapy device 102. Representative knowledge workers include healthcare providers 130, the device manufacturer 132, clinical groups 134, and regulatory agencies 136. The knowledge workers are interested in different portions of the data. For instance, the healthcare providers 130 are interested in information pertaining to a particular patient's condition. The manufacturer 132 cares about how the device is operating. The clinical groups 134 want certain data for inclusion in patient populations that can be studied and analyzed. The regulatory agencies 136 are concerned whether the devices, and various treatments administered by them, are safe or pose a health risk.

The network architecture 100 facilitates distribution of the device data to the various knowledge workers. Information gathered from the device is integrated, processed, and distributed to the knowledge workers. Computer systems maintain and store the device data, and prepare the data for efficient presentation to the knowledge workers. The computer systems are represented pictorially in FIG. 1 as databases. However, such system can be implemented using a wide variety of computing devices, ranging from small handheld computers or portable digital assistants (PDAs) carried by physicians to workstations or mainframe computers with large storage capabilities.

The healthcare providers 130 are equipped with computer systems 140 that store and process patient records 142. The manufacturer 132 has a computer system 144 that tracks device data 146 returned from ICTDs 102. The clinical groups 134 have computer systems 148 that store and analyze data across patient populations, as represented by a histogram 150. The regulatory agencies 136 maintain computer systems 152 that register and track healthcare risk data 154 for ICTDs.

The network architecture 100 supports two-way communication. Not only is data collected from the ICTD 102 and distributed to the various computer systems of the knowledge workers, but also information can be returned from these computer systems to the networked programmer 114 and/or the local transceiver 112 for communication back to the ICTD 102. Information returned to the ICTD 102 may be used to adjust operation of the device, or modify therapies being applied by the device. Such information may be imparted to the ICTD 102 automatically, without the patient's knowledge.

Notifications

Information may also be sent to a patient notification device 160 to notify the patient of some event or item. This information may be notification messages. These messages may include instructions to contact their healthcare provider, instructions on how/where to visit the closest healthcare provider to them, information regarding device status, information regarding patient status, information about impending or predicted health events, warnings about current patient health status, information regarding a recent patient episode, etc.

The patient notification device 160 may be implemented in a number of ways including, for example, as a telephone, a cellular phone, a satellite phone, instant messaging, a fax, a pager, a PDA (personal digital assistant), a dedicated patient communication device, a computer, an alarm, and so on. Notifications may be as simple as an instruction to sound an alarm to inform the patient to call into the healthcare providers, or as complex as HTML-based pages with graphics and textual data to educate the patient.

Notification messages sent to the patient notification device 160 can contain essentially any type of information related to cardiac medicinal purposes or device operation. Such information might include new studies released by clinical groups pertaining to device operation and patient activity (e.g., habits, diets, exercise, etc.), recall notices or operational data from the manufacturer, patient-specific instructions sent by the healthcare providers, or warnings published by regulatory groups.

Notifications can be sent directly from the knowledge worker to the patient. Additionally, the network architecture 100 may include a notification system 170 that operates computer systems 172 designed to create and deliver notification messages 174 on behalf of the knowledge workers. The notification system 170 delivers the messages in formats supported by the various types of patient notification devices 160. For instance, if the patient carries a pager, a notification message might consist of a simple text statement in a pager protocol. For a more sophisticated wireless-enabled PDA or Internet-oriented cellular phone, messages might contain more than text data and be formatted using WAP formats.

Flow of Data

Figure 2:
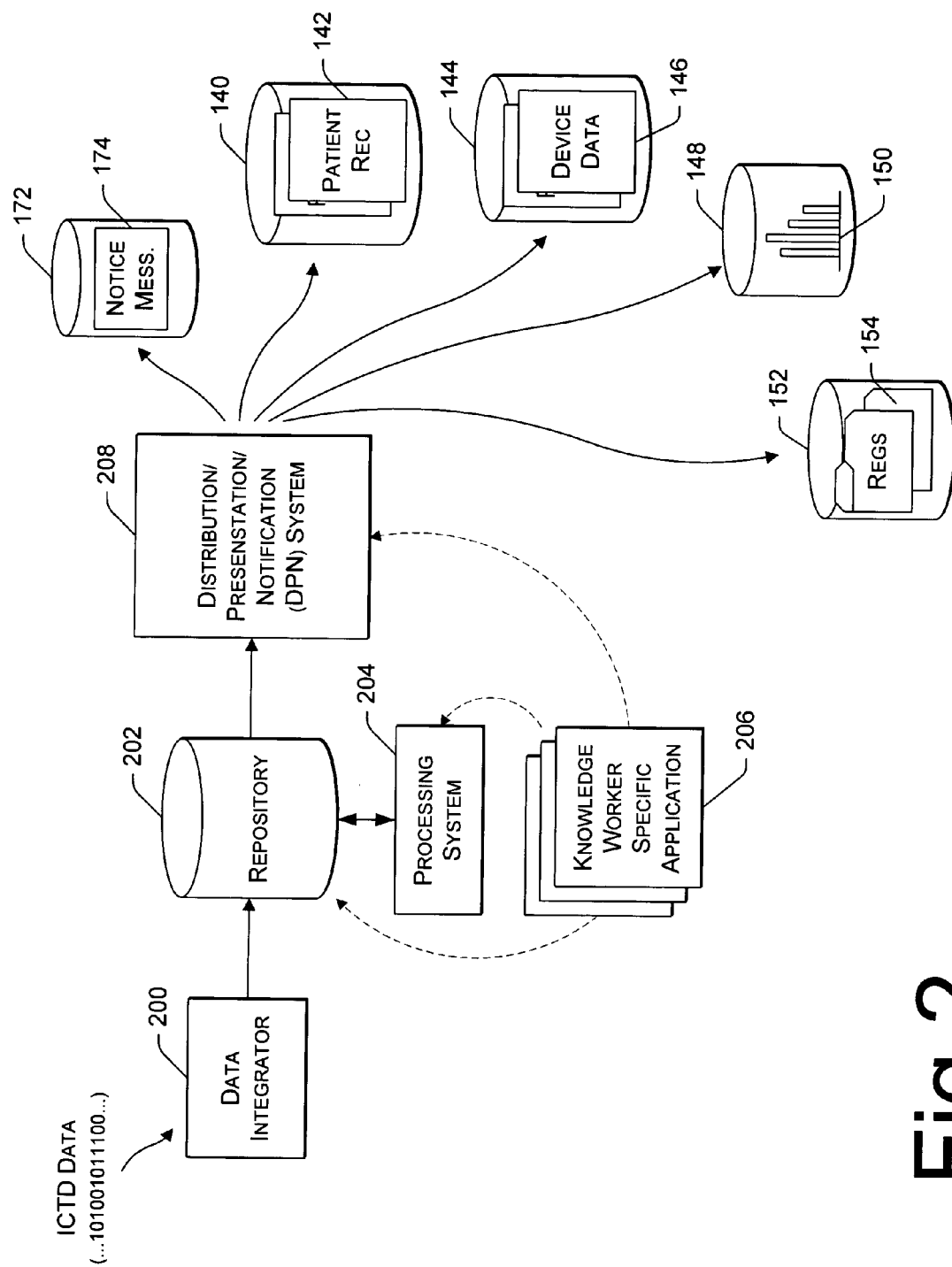
FIG. 2 is a functional diagram illustrating information flow from the ICTD to the computing systems associated with the knowledge workers.

FIG. 2 shows the flow of data from the ICTD 102 to the various computer systems used by the knowledge workers. Data from the ICTD is output as digital data, as represented by the string of 0's and 1's. The data may consist of any number of items, including heart activity (e.g., internal electrograms, EGMs), patient information, device operation, analysis results from on-device diagnostics, and so on.

A data integrator 200 accumulates the data and stores it in a repository 202. A processing system 204 processes portions of the data according to various applications 206 that are specifically tailored to place the data into condition for various knowledge workers. For example, healthcare workers might be interested in certain portions of the data, such as the EGM data and the patient information. Clinical scientists might be interested in the heart data, but do not wish to see any patient identifying information. Manufacturers may be interested in the raw data stream itself as a tool to discern how the device is operating. Depending on the needs of the end worker, the processing system 204 takes the raw device data, evaluates its accuracy and completeness, and generates different packages of data for delivery to the various knowledge workers. The processed data packages are also stored in the repository 202.

When the data is ready for delivery, a distribution/presentation/notification system 208 (or DPN system) distributes the different packages to the appropriate computer systems 140, 144, 148, 152, and 172. The DPN system 208 is configured to serve the packages according to the protocols and formats desired by the computer systems. In this manner, the network architecture 100 allows relevant portions of device data, collected from the ICTD, to be disseminated to the appropriate knowledge workers in a form they prefer.

Once the ICTD data is delivered, the computer systems 140, 144, 148, 152, and 172 store the data and/or present the data to the knowledge worker. The computer systems may perform further processing specific to their use of the data. Through these processes, the knowledge workers create additional information that is useful to the patient, or other knowledge workers with interests in ICTDs. For example, from the ICTD data, the knowledge workers might devise improved therapies for a given patient, or create instructions to modify operation of a specific ICTD, or gain a better understanding of how implantable cardiac devices operate in general, or develop better technologies for future generations of ICTDs. Much of this created knowledge can be shared among the various knowledge workers.

Information Sharing

Figure 3:
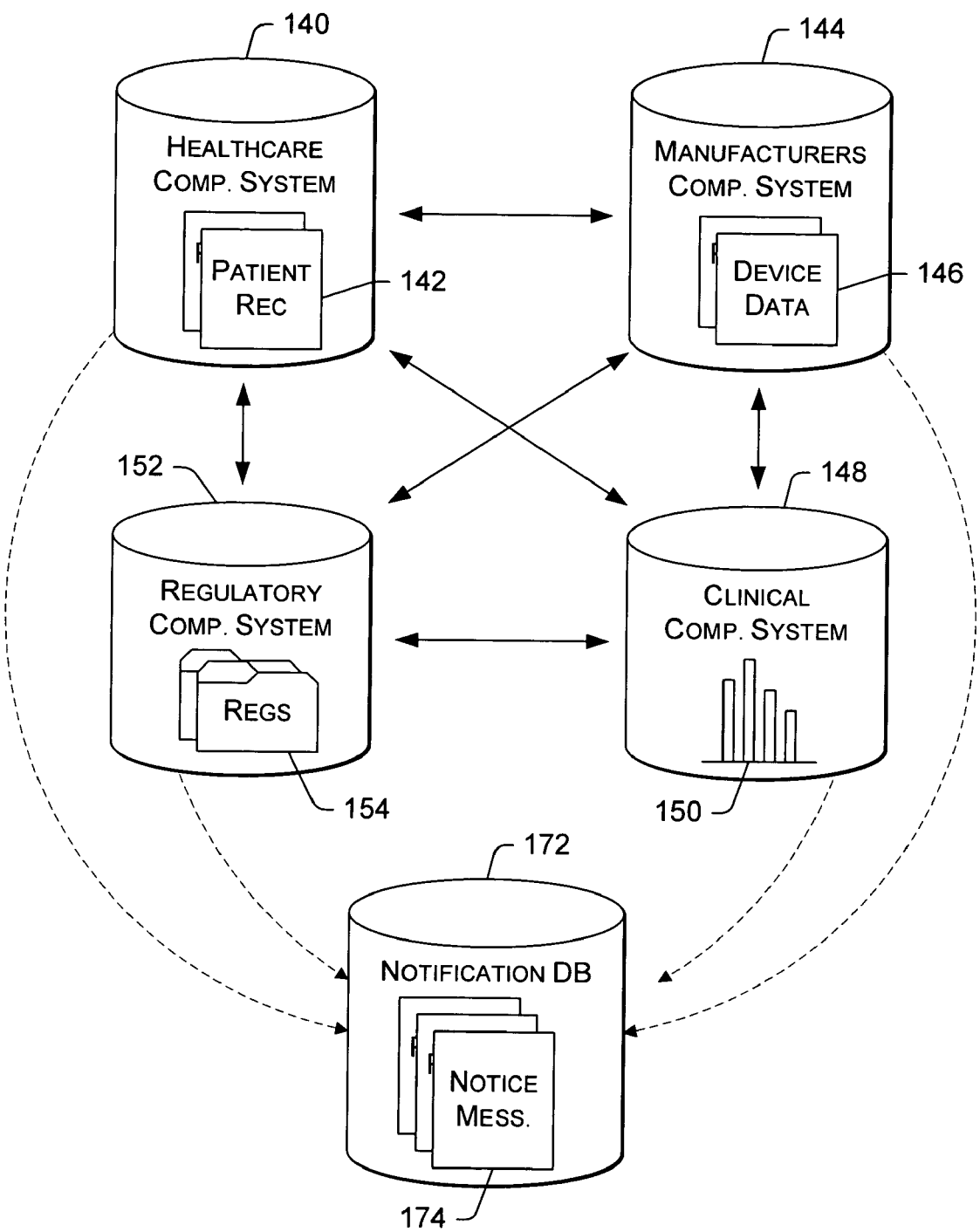
FIG. 3 is a functional diagram illustrating how the various computing systems share pieces of information to improve care given to the patient.

FIG. 3 shows how the various computing systems 140, 144, 148, 152, and 172 can cooperate and share pieces of information to improve the care given to a patient. Where appropriate and legally acceptable, the computer systems may be configured to pass non-private information among the various knowledge workers to better improve their understanding of the implantable medical field. Clinical results 150 produced by the clinical computer systems 148 may be shared with healthcare providers to improve patient care or with manufacturers to help in their design of next generation devices. The sharing of information may further lead to better and timelier healthcare for the patients. If the collective knowledge base produces information that may prove helpful to the patient, that information can be passed to the notification system 172 for delivery to one or more patients. Also, any one of the knowledge workers may wish to employ the notification system 172 to send messages to the patient(s).

Patient Feedback Architecture

Figure 4:
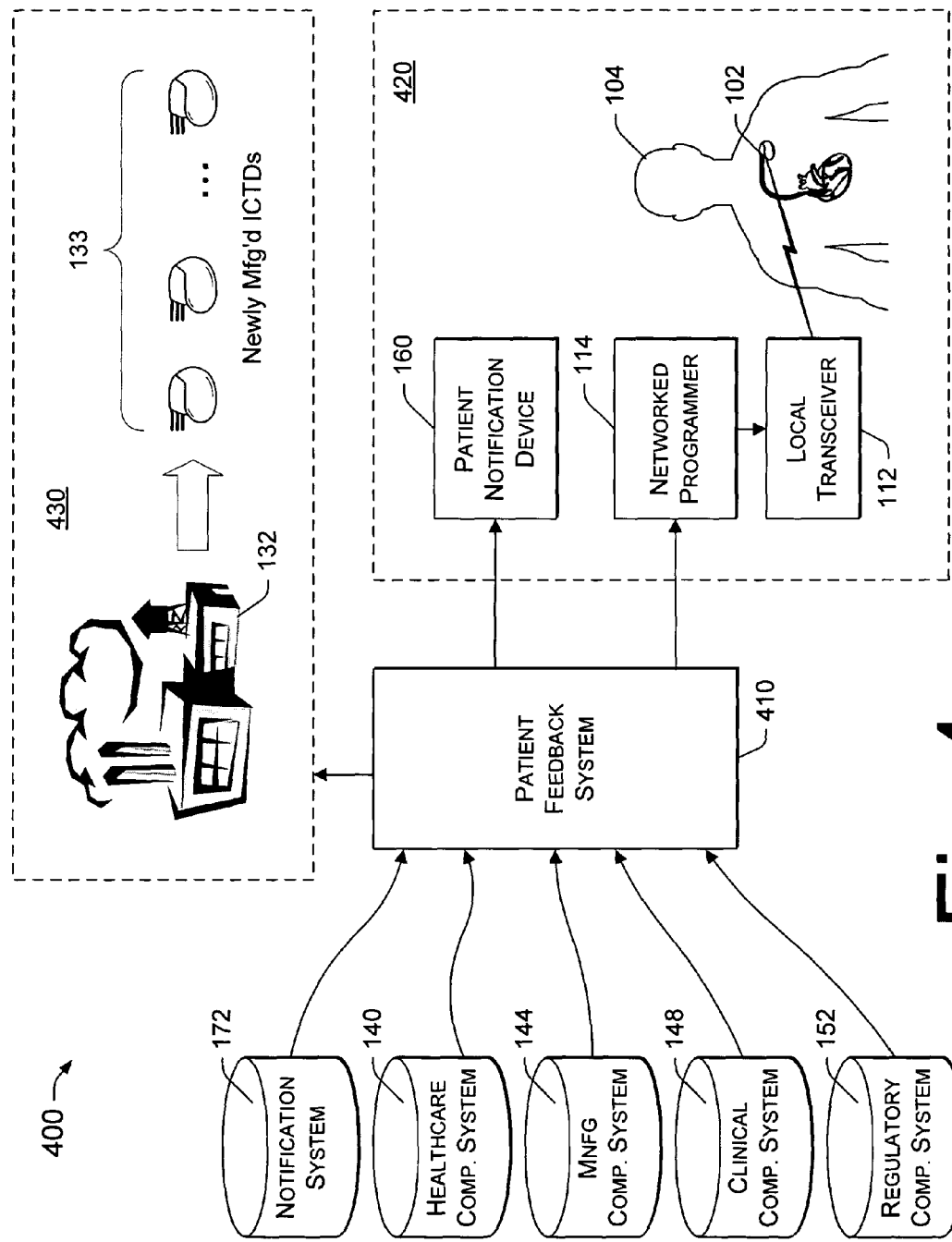
FIG. 4 is a functional diagram illustrating information flow from the computing systems back to the ICTD.

FIG. 4 shows, in more detail, the flow of information back from the various computer systems used by the knowledge workers to the implantable cardiac therapy device 102 or the patient notification device 160. Information from any one of the computing systems—healthcare computer system(s) 140, manufacturer computer system(s) 144, clinical computer system(s) 148, regulatory computer system(s) 152—or the notification system 172 can be sent to a patient feedback system 400. The patient feedback system 400 facilitates delivery of the information back to the patient. It may be an independent system, or incorporated into one or more of the computing. It may alternatively be integrated into the notification system 172.

The patient feedback system 400 may be implemented in many ways. As one exemplary implementation, the patient feedback system 400 is implemented as a server that serves content back to the networked programmer 114, which then uses the information to program the ICTD 102 through a built in transceiver 116, local transceiver 112, or wand-based telemetry. As another possible implementation, the patient feedback system may be a cellular or RF transmission system that sends information back to the patient feedback device 160.

The network architecture 100 facilitates continuous care around the clock, regardless of where the patient is located. For instance, suppose the patient is driving in the car when a cardiac episode occurs. The ICTD 102 detects the condition and transmits an alert message about the condition to the local transceiver 112. The message is processed and delivered to a physician's computer or PDA via the network 120. The physician can make a diagnosis and send some instructions back to the patient's ICTD. The physician might also have a notification message that guides the patient to a nearest healthcare facility for further treatment sent via the notification system 170 to the patient's notification device 160. Concurrently, the physician can share the patient's records online with an attending physician at the healthcare facility so that the attending physician can review the records prior to the patient's arrival.

Exemplary ICTD

Figure 5:
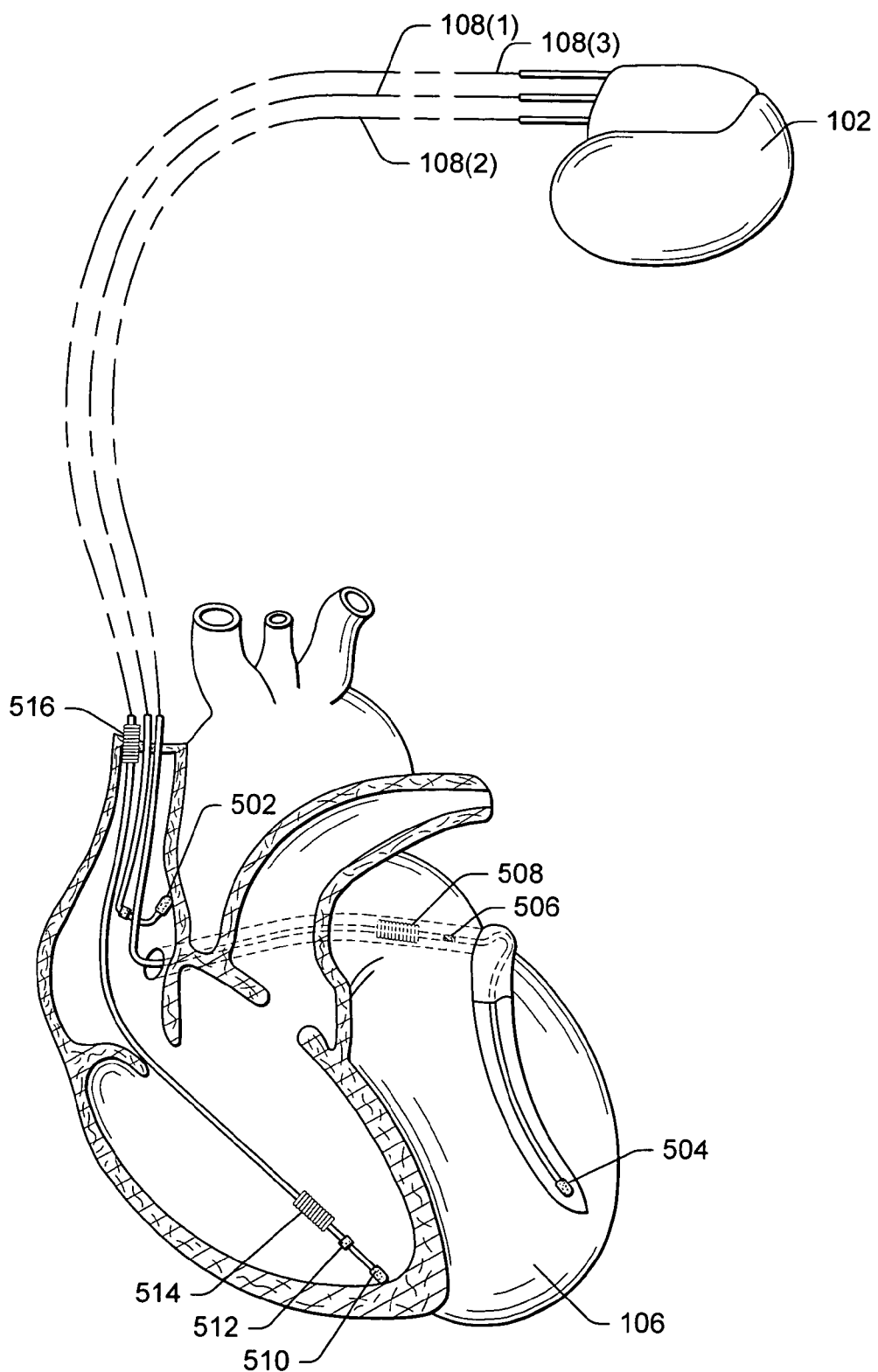
FIG. 5 is a simplified illustration of an ICTD in electrical communication with a patient's heart for monitoring heart activity and/or delivering stimulation therapy.

FIG. 5 shows an exemplary ICTD 102 in electrical communication with a patient's heart 106 for monitoring heart activity and/or delivering stimulation therapy, such as pacing or defibrillation therapies. The ICTD 102 is in electrical communication with a patient's heart 106 by way of three leads 108(1)-(3). To sense atrial cardiac signals and to provide right atrial chamber stimulation therapy, the ICTD 102 is coupled to an implantable right atrial lead 108(1) having at least an atrial tip electrode 502, which typically is implanted in the patient's right atrial appendage. To sense left atrial and ventricular cardiac signals and to provide left chamber pacing therapy, the ICTD 102 is coupled to a coronary sinus lead 108(2) designed for placement in the coronary sinus region via the coronary sinus. The coronary sinus lead 108(2) positions a distal electrode adjacent to the left ventricle and/or additional electrode(s) adjacent to the left atrium. An exemplary coronary sinus lead 108(2) is designed to receive atrial and ventricular cardiac signals and to deliver left ventricular pacing therapy using at least a left ventricular tip electrode 504, left atrial pacing therapy using at least a left atrial ring electrode 506, and shocking therapy using at least a left atrial coil electrode 508.

The ICTD 102 is also shown in electrical communication with the patient's heart 106 by way of an implantable right ventricular lead 108(3) having, in this implementation, a right ventricular tip electrode 510, a right ventricular ring electrode 512, a right ventricular (RV) coil electrode 514, and an SVC coil electrode 516. Typically, the right ventricular lead 108(3) is transvenously inserted into the heart 102 to place the right ventricular tip electrode 510 in the right ventricular apex so that the RV coil electrode 514 will be positioned in the right ventricle and the SVC coil electrode 516 will be positioned in the superior vena cava. Accordingly, the right ventricular lead 108(3) is capable of receiving cardiac signals, and delivering stimulation in the form of pacing and shock therapy to the right ventricle.

Figure 6:
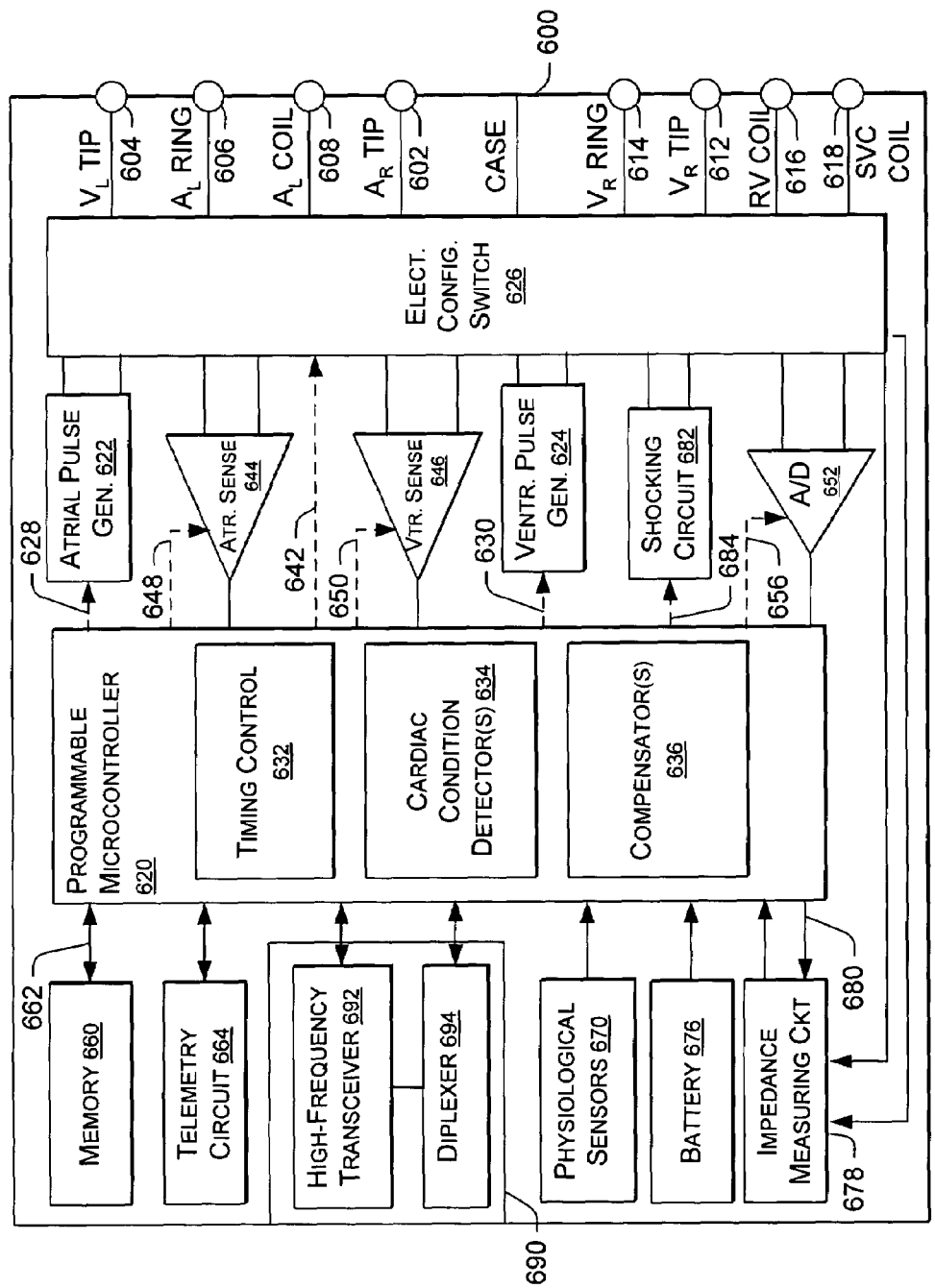
FIG. 6 is a functional block diagram of an exemplary implantable cardiac therapy device.

FIG. 6 shows an exemplary, simplified block diagram depicting various components of the ICTD 102. The ICTD 102 can be configured to perform one or more of a variety of functions including, for example, monitoring heart activity, monitoring patient activity, and treating fast and slow arrhythmias with stimulation therapy that includes cardioversion, defibrillation, and pacing stimulation. While a particular multi-chamber device is shown, it is to be appreciated and understood that this is done for illustration purposes.

The circuitry is housed in housing 600, which is often referred to as the "can", "case", "encasing", or "case electrode", and may be programmably selected to act as the return electrode for unipolar modes. Housing 600 may further be used as a return electrode alone or in combination with one or more of the coil electrodes for shocking purposes. Housing 600 further includes a connector (not shown) having a plurality of terminals 602, 604, 606, 608, 612, 614, 616, and 618 (shown schematically and, for convenience, the names of the electrodes to which they are connected are shown next to the terminals).

To achieve right atrial sensing and pacing, the connector includes at least a right atrial tip terminal (AR TIP) 602 adapted for connection to the atrial tip electrode 502. To achieve left chamber sensing, pacing, and shocking, the connector includes at least a left ventricular tip terminal (VL TIP) 604, a left atrial ring terminal (AL RING) 606, and a left atrial shocking terminal (AL COIL) 608, which are adapted for connection to the left ventricular ring electrode 504, the left atrial ring electrode 506, and the left atrial coil electrode 508, respectively. To support right chamber sensing, pacing, and shocking, the connector includes a right ventricular tip terminal (VR TIP) 612, a right ventricular ring terminal (VR RING) 614, a right ventricular shocking terminal (RV COIL) 616, and an SVC shocking terminal (SVC COIL) 618, which are adapted for connection to the right ventricular tip electrode 510, right ventricular ring electrode 512, the RV coil electrode 514, and the SVC coil electrode 516, respectively.

At the core of the ICTD 102 is a programmable microcontroller 620 that controls various operations of the ICTD, including cardiac monitoring and stimulation therapy. Microcontroller 620 includes a microprocessor (or equivalent control circuitry), RAM and/or ROM memory, logic and timing circuitry, state machine circuitry, and I/O circuitry. Microcontroller 620 includes the ability to process or monitor input signals (data) as controlled by a program code stored in a designated block of memory. Any suitable microcontroller 620 may be used. The use of microprocessor-based control circuits for performing timing and data analysis functions are well known in the art.

For discussion purposes, microcontroller 620 is illustrated as including timing control circuitry 632 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, and so on. Microcontroller 220 may further include various types of cardiac condition detectors 634 (e.g., an arrhythmia detector, a morphology detector, etc.) and various types of compensators 636 (e.g., orthostatic compensator, syncope response module, etc.). These components can be utilized by the device 102 for determining desirable times to administer various therapies. The components 632–636 may be implemented in hardware as part of the microcontroller 620, or as software/firmware instructions programmed into the device and executed on the microcontroller 620 during certain modes of operation.

The ICTD 102 further includes an atrial pulse generator 622 and a ventricular pulse generator 624 that generate pacing stimulation pulses for delivery by the right atrial lead 108(1), the coronary sinus lead 108(2), and/or the right ventricular lead 108(3) via an electrode configuration switch 626. It is understood that in order to provide stimulation therapy in each of the four chambers of the heart, the atrial and ventricular pulse generators, 622 and 624, may include dedicated, independent pulse generators, multiplexed pulse generators, or shared pulse generators. The pulse generators 622 and 624 are controlled by the microcontroller 620 via appropriate control signals 628 and 630, respectively, to trigger or inhibit the stimulation pulses.

The electronic configuration switch 626 includes a plurality of switches for connecting the desired electrodes to the appropriate I/O circuits, thereby providing complete electrode programmability. Accordingly, switch 626, in response to a control signal 642 from the microcontroller 620, determines the polarity of the stimulation pulses (e.g., unipolar, bipolar, combipolar, etc.) by selectively closing the appropriate combination of switches (not shown).

Atrial sensing circuits 644 and ventricular sensing circuits 646 may also be selectively coupled to the right atrial lead 108(1), coronary sinus lead 108(2), and the right ventricular lead 108(3), through the switch 626 to detect the presence of cardiac activity in each of the four chambers of the heart. Accordingly, the atrial (ATR. SENSE) and ventricular (VTR. SENSE) sensing circuits, 644 and 646, may include dedicated sense amplifiers, multiplexed amplifiers, or shared amplifiers. Each sensing circuit 644 and 646 may further employ one or more low power, precision amplifiers with programmable gain and/or automatic gain control, bandpass filtering, and a threshold detection circuit to selectively sense the cardiac signal of interest. The automatic gain control enables the ICTD 102 to deal effectively with the difficult problem of sensing the low amplitude signal characteristics of atrial or ventricular fibrillation. Switch 626 determines the "sensing polarity" of the cardiac signal by selectively closing the appropriate switches. In this way, the clinician may program the sensing polarity independent of the stimulation polarity. The outputs of the atrial and ventricular sensing circuits 644 and 646 are connected to the microcontroller 620 which, in turn, is able to trigger or inhibit the atrial and ventricular pulse generators 622 and 624, respectively, in a demand fashion in response to the absence or presence of cardiac activity in the appropriate chambers of the heart. The sensing circuits 644 and 646 receive control signals over signal lines 648 and 650 from the microcontroller 620 for purposes of controlling the gain, threshold, polarization charge removal circuitry (not shown), and the timing of any blocking circuitry (not shown) coupled to the inputs of the sensing circuits 644 and 646.

Cardiac signals are also applied to inputs of an analog-to-digital (A/D) data acquisition system 652. The data acquisition system 652 is configured to acquire intracardiac electrogram signals, convert the raw analog data into a digital signal, and store the digital signals for later processing and/or telemetric transmission to an external device 654. The data acquisition system 652 is coupled to the right atrial lead 108(1), the coronary sinus lead 108(2), and the right ventricular lead 108(3) through the switch 626 to sample cardiac signals across any pair of desired electrodes.

The data acquisition system 652 may be coupled to the microcontroller 620, or other detection circuitry, to detect an evoked response from the heart 106 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 620 detects a depolarization signal during a window following a stimulation pulse, the presence of which indicates that capture has occurred. The microcontroller 620 enables capture detection by triggering the ventricular pulse generator 624 to generate a stimulation pulse, starting a capture detection window using the timing control circuitry 632 within the microcontroller 620, and enabling the data acquisition system 652 via control signal 656 to sample the cardiac signal that falls in the capture detection window and, based on the amplitude, determines if capture has occurred.

The microcontroller 620 is further coupled to a memory 660 by a suitable data/address bus 662, wherein the programmable operating parameters used by the microcontroller 620 are stored and modified, as required, in order to customize the operation of the implantable device 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 106 within each respective tier of therapy. With memory 660, the ICTD 102 is able to sense and store a relatively large amount of data (e.g., from the data acquisition system 652), which may transmitted to the external network of knowledge workers for subsequent analysis.

Operating parameters of the ICTD 102 may be non-invasively programmed into the memory 660 through a telemetry circuit 664 in telemetric communication with an external device, such as a programmer 110 or local transceiver 112. The telemetry circuit 664 advantageously allows intracardiac electrograms and status information relating to the operation of the device 102 (as contained in the microcontroller 620 or memory 660) to be sent to the external devices.

The ICTD 102 can further include one or more physiologic sensors 670, commonly referred to as "rate-responsive" sensors because they are typically used to adjust pacing stimulation rate according to the exercise state of the patient. However, the physiological sensor 670 may further be used to detect changes in cardiac output, changes in the physiological condition of the heart, or diurnal changes in activity (e.g., detecting sleep and wake states, detecting position or postural changes, etc.). Accordingly, the microcontroller 620 responds by adjusting the various pacing parameters (such as rate, AV Delay, V—V Delay, etc.) at which the atrial and ventricular pulse generators, 622 and 624, generate stimulation pulses. While shown as being included within the device 102, it is to be understood that the physiologic sensor 670 may also be external to the device 102, yet still be implanted within or carried by the patient. Examples of physiologic sensors that may be implemented in device 102 include known sensors that, for example, sense respiration rate and/or minute ventilation, pH of blood, ventricular gradient, and so forth.

The ICTD 102 additionally includes a battery 676 that provides operating power to all of circuits shown in FIG. 2. If the device 102 is configured to deliver pacing or shocking therapy, the battery 676 is capable of operating at low current drains for long periods of time (e.g., preferably less than 10 □A), and is capable of providing high-current pulses (for capacitor charging) when the patient requires a shock pulse (e.g., preferably, in excess of 2 A, at voltages above 2 V, for periods of 10 seconds or more). The battery 676 also desirably has a predictable discharge characteristic so that elective replacement time can be detected. As one example, the device 102 employs lithium/silver vanadium oxide batteries.

The ICTD 102 can further include magnet detection circuitry (not shown), coupled to the microcontroller 620, to detect when a magnet is placed over the device 102. A magnet may be used by a clinician to perform various test functions of the device 102 and/or to signal the microcontroller 620 that the external programmer is in place to receive or transmit data to the microcontroller 620 through the telemetry circuits 664. The ICTD 102 further includes an impedance measuring circuit 678 that is enabled by the microcontroller 620 via a control signal 680. Uses for an impedance measuring circuit 678 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 678 is advantageously coupled to the switch 626 so that any desired electrode may be used.

In the case where the device 102 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 620 further controls a shocking circuit 682 by way of a control signal 684. The shocking circuit 682 generates shocking pulses of low (up to 0.5 Joules), moderate (0.5–10 Joules), or high energy (11 to 40 Joules), as controlled by the microcontroller 620. Such shocking pulses are applied to the patient's heart 106 through at least two shocking electrodes, and as shown in this implementation, selected from the left atrial coil electrode 508, the RV coil electrode 514, and/or the SVC coil electrode 516. As noted above, the housing 600 may act as an active electrode in combination with the RV coil electrode 514, or as part of a split electrical vector using the SVC coil electrode 516 or the left atrial coil electrode 508 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 620 is capable of controlling the synchronous or asynchronous delivery of the shocking pulses. The ICTD 102 may further be designed with the ability to support high-frequency wireless communication, typically in the radio frequency (RF) range. As illustrated in FIG. 2, the can 600 may be configured with a secondary, isolated casing 690 that contains circuitry for handling high-frequency signals. Within this separate case 690 are a high-frequency transceiver 692 and a diplexer 694. High-frequency signals received by a dedicated antenna, or via leads 108, are passed to the transceiver 692. Due to the separate casing region 690, the transceiver handles the high-frequency signals in isolation apart from the cardiac therapy circuitry. In this manner, the high-frequency signals can be safely handled, thereby improving telemetry communication, without adversely disrupting operation of the other device circuitry.

Exemplary Computing Device

Figure 7:
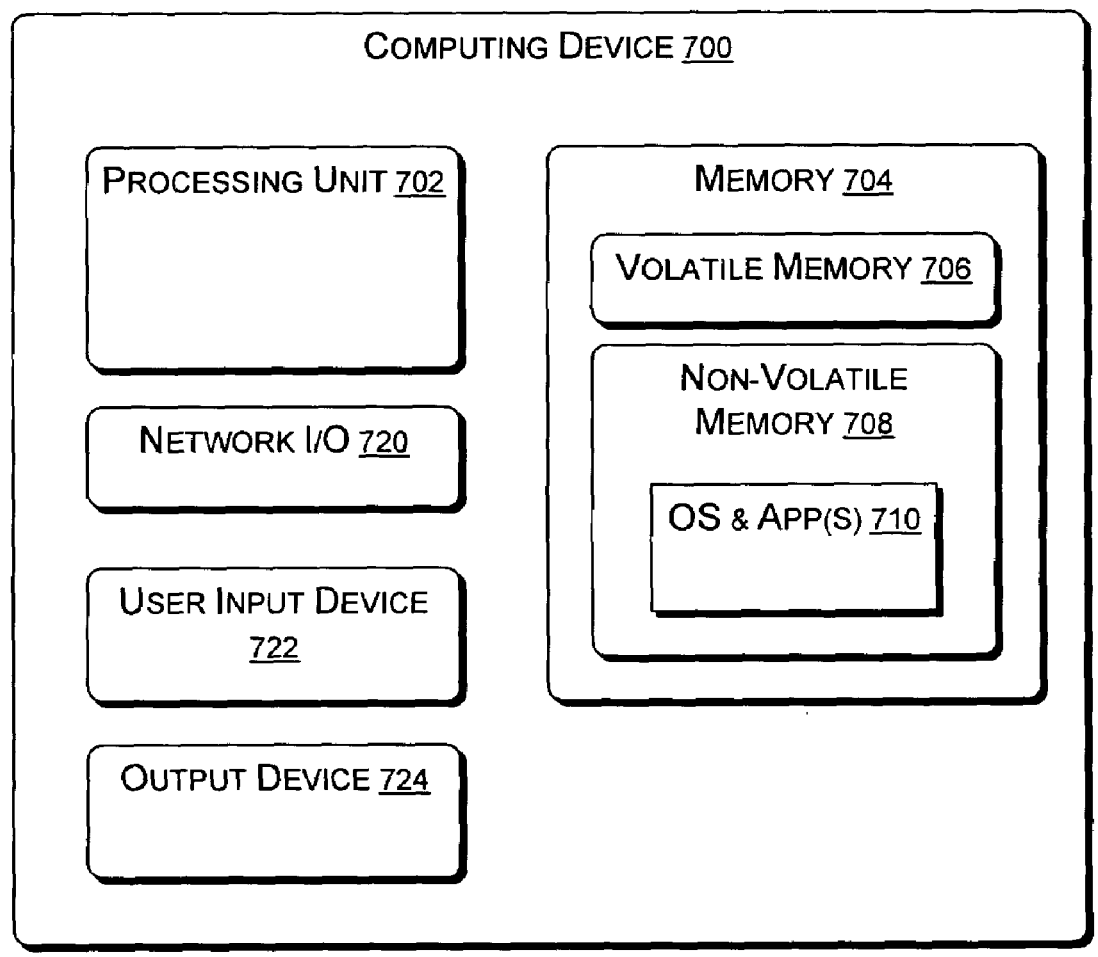
FIG. 7 is a functional block diagram of an exemplary computing device that may be used in the computing systems of the cardiac therapy network architecture.

FIG. 7 shows an exemplary computing device 700 employed in the computing systems of the cardiac therapy network architecture 100. It includes a processing unit 702 and memory 704. Memory 704 includes both volatile memory 706 (e.g., RAM) and non-volatile memory 708 (e.g., ROM, EEPROM, Flash, disk, optical discs, persistent storage, etc.). An operating system and various application programs 710 are stored in non-volatile memory 708. When a program is running, various instructions are loaded into volatile memory 706 and executed by processing unit 702. Examples of possible applications that may be stored and executed on the computing device include the knowledge worker specific applications 206 shown in FIG. 2.

The computing device 700 may further be equipped with a network I/O connection 720 to facilitate communication with a network. The network I/O 720 may be a wire-based connection (e.g., network card, modem, etc.) or a wireless connection (e.g., RF transceiver, Bluetooth device, etc.). The computing device 700 may also include a user input device 722 (e.g., keyboard, mouse, stylus, touch pad, touch screen, voice recognition system, etc.) and an output device 724 (e.g., monitor, LCD, speaker, printer, etc.).

Various aspects of the methods and systems described throughout this disclosure may be implemented in computer software or firmware as computer-executable instructions. When executed, these instructions direct the computing device (alone, or in concert with other computing devices of the system) to perform various functions and tasks that enable the cardiac therapy network architecture 100.

Notification Architecture

One feature of the network architecture is a notification architecture that enables a comprehensive, integrated, efficient, effective, and quick mechanism for notifying an ICTD patient. Such notifications may be sent manually from a knowledge worker to the patient. Alternatively, such notifications may be automatically generated based upon one or more triggering events or determinations.

The notification architecture places the notification data in a suitable format and protocol to accommodate different types of notification receiving devices with different UI capabilities. The notification architecture separates the processing and notification functions so that decisions regarding how to present the content are made independently of the collection and processing of the data.

Figure 8:
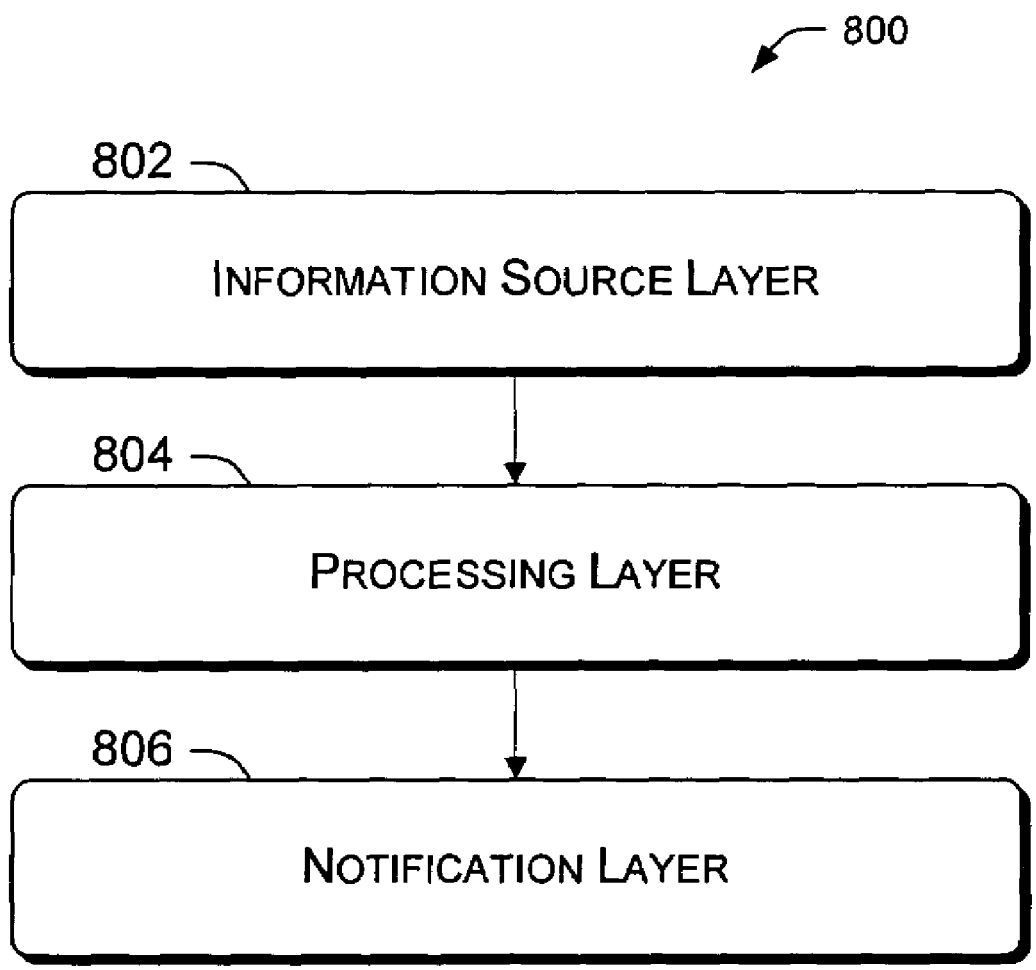
FIG. 8 illustrates a notification architecture implemented by the network architecture to facilitate distribution and notification of notification messages to the ICTD patients.

FIG. 8 shows the notification architecture 800 that is implemented by the network architecture. The notification architecture 800 has three layers: an information source layer 802, a processing layer 804, and a notification layer 806. The information source layer 802 provides the data or information that is to be processed. This layer includes data output by the ICTD, such as heart activity (e.g., IEGM), patient information, device operation data, analysis results from on-device diagnostics, and so on. It may further include other information made available for purposes of processing or better understanding the ICTD data.

The processing layer 804 performs the data handling and analytical processes. The processing layer 804 may include, for example, the processing system 204 and applications 206 that create the content desired by the ICTD patient.

The notification layer 806 is responsible for getting the content to the ICTD patient in a form they prefer. This layer 806 contains the applications and processes that determine which content to present to whom, the format of the content, and the protocol by which to send the content.

Figure 9:
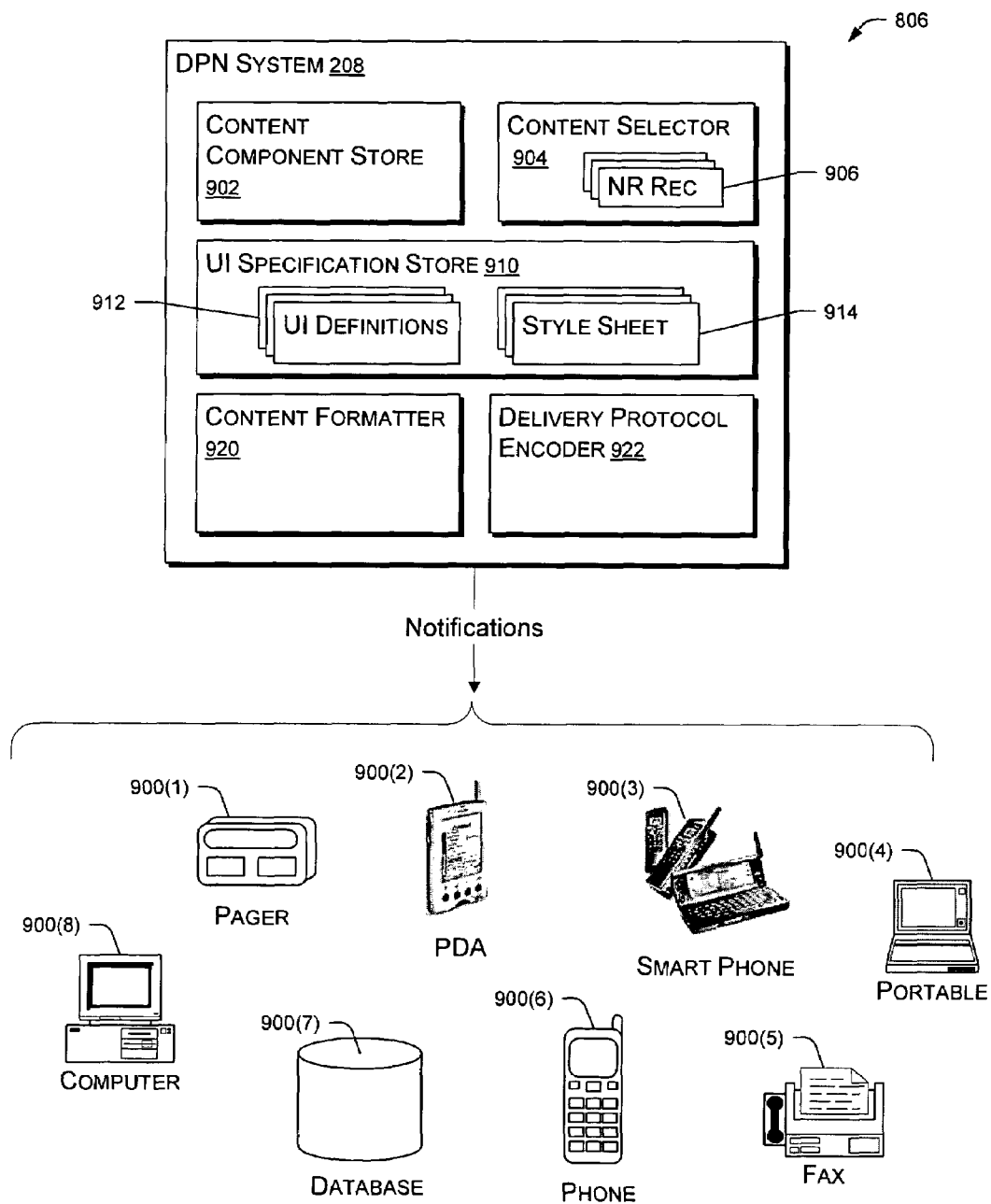
FIG. 9 is a functional block diagram of an exemplary notification system.

FIG. 9 shows one exemplary implementation of the notification layer 806 configured as the DPN system 208. The notification layer 806 enables effective delivery and notification of content to many different types of notification devices, as represented by exemplary devices 900(1)-(8). It is anticipated that ICTD patients will utilize many diverse types of notification devices, including pagers 900(1), personal digital assistants (PDAs) 900(2), Web-enabled or "smart" phones 900(3), portable computers 900(4), facsimile machines 900(5), cellular phones 900(6), databases 900(7), and desktop computers 900(8). These devices may be implemented using open standard software and protocols, or proprietary software and protocols.

The notification layer 806 includes a content component store 902 to store snippets of content ready for notification to the ICTD patients. The content may include raw data, processed data, pre-defined messages, additional information added during processing, and so on. Although the content store 902 is illustrated in FIG. 9 as residing at the DPN system 208, it may also reside in the repository 202. The notification layer 806 may further include a content selector 904 to choose the content components from store 902 for notification to the various ICTD patients. For instance, the content selector 904 may select pre-defined patient-specific message (e.g., "call doctors office immediately at 555-1234", "go to the emergency room", etc.). It might further choose device-related information (e.g., raw IEGM data) for notification to the manufacturer.

The content selector 904 maintains a set of to-be-notified records 906 in a database or other storage unit. The to-be-notified may include, for example, the ICTD patients and the device manufacturer. The records 906 specify the contact information, information preferences, and computing resources. The records 906 track, for example, the contact's email address, phone numbers, and pager numbers. The records 906 might further specify the type of desired information and the type(s) of notification devices 900 used. As one example, a record 906 for an ICTD patient may specify the contact information, the patient's preference to see emergency messages, and that the primary computing device is a Palm Pilot® PDA 900(2) with wireless communication capabilities but limited UI features.

A user interface (UI) specification store 910 maintains the rules that dictate how the content is to be presented on different notification devices and software platforms. The notification devices 900(1)-(7) have a wide variety of UI features and capabilities, ranging from high-resolution color monitors, to single-line LCD displays or audio alarms, to database structures and facsimile machines.

The UI specification store 910 maintains one or more UI definitions 912 that specify device requirements for visual/audio output. The UI definitions 912 include such parameters of whether devices have a display and if so, the display type (e.g., LCD, CRT, LED, etc.), display size, whether the display is capable of showing graphics and/or color, whether audio is possible, and so on. These UI definitions 912 help the content selector 904 identify which snippets of information in the content store 902 should be selected for a given device specified in the receiver's record 906.

The UI specification store 910 also includes one or more style sheets 914 that specify how the content is to be arranged for a given computing device. The style sheets 914 specify the format of the information, such as HTML, XML, SNMP (Simple Network Management Protocol), etc. The sheets also dictate the type of content that can be included, such as graphical components, text, audio, video, and so on. The notification layer 806 might also include a content formatter 920 to place the content into the appropriate format specified by the UI specification store 910 for a target computing device. For instance, if a particular patient utilizes a laptop computer that is capable of receiving HTML documents, the content formatter 920 formats the content in HTML for effective notification. If another patient has a cellular phone, the content formatter 920 may format the content text that can be readily depicted on a limited display.

A delivery protocol encoder 922 encodes the formatted content according to the protocols supported by the notification devices and networks used by the notification receiver. There are many possible protocols, including HTTP, TCP/IP, WAP, Bluetooth, etc. Depending upon the preferences specified in the notification receiver records 906, the delivery protocol encoder 922 encodes the content to the appropriate delivery protocol for subsequent distribution to the devices operated by the notification receiver.

Separating the notification and processing layers and implementing UI definitions and style sheets enables the architecture to distribute content produced by multiple applications to a wide assortment of notification devices without requiring unique UIs for each computing device. Suppose there are three applications that produce content to be distributed to four different notification devices of the notification receiver. If the notification layer were integrated with the processing layer, the application developer would need to write a specific UI for each device, resulting in twelve different versions of UI code (i.e., the number of applications times the number of devices).

By separating the notification layer, however, independent UI definitions 912(1)-(3) can be developed to specify UI requirements imposed by individual applications. Style sheets 910(1)-(4) can be created to describe what features individual devices are able to support. Combining the UI definition with a style sheet dictates what content sent for notification and how it is presented for a given computing device. In this example, the architecture allows, at most, the creation of seven definitions/sheets to facilitate notification of content from three applications on four devices (i.e., the number of applications plus the number of devices), down from twelve separate versions.

This architecture is easily adopted to support new notification devices. A developer defines a new UI definition and/or a style sheet to enable notification of content on the new device. This saves time and money in that developers are not forced to modify applications as UI capabilities of the end-user notification devices change.

Notification Operation

Figure 10:
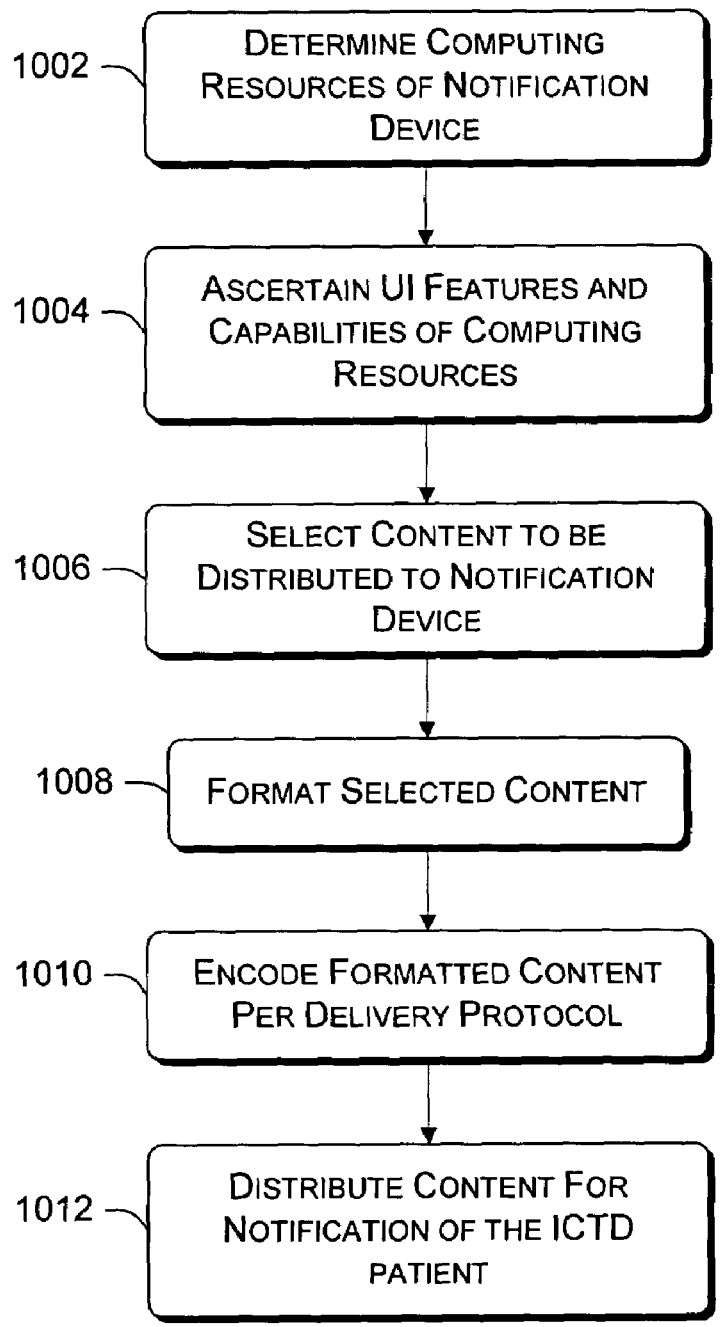
FIG. 10 is a flow diagram of a methodological implementation of a notification system.

FIG. 10 shows methodological implementation of the exemplary notification system performed by the cardiac therapy network architecture 100 (or some portion thereof). This methodological implementation may be performed in software, hardware, or a combination thereof.

At block 1002, the DPN system 208 determines what computing resources are available for the notification receiver who is intended to receive the information. The system consults the notification receiver records 906 to identify the types of notification devices specified by the notification receiver. At block 1004, the system ascertains the features and capabilities of the computing resources of the intended notification receiver. Such features may include display type, display size, graphical capabilities, color capabilities, etc.

At block 1006, the content selector 904 selects the content to be delivered to the notification receiver based, in part, on the capabilities of the computing resources. For instance, if the ICTD patient is carrying a PDA or phone of limited screen size, the content selector 904 extracts summary statements or phrases from the content component store 902 that can be presented on the device. For instance, the content selector might choose a statement "Recommend to take X dosage of Y within 15 minutes.

At block 1008, the content formatter 920 formats the selected content into suitable formats for transmission to the notification receiver's computing device. Examples of possible formats include plain text, HTML, XML, and SNMP.

At block 1010, the delivery protocol encoder 922 encodes the content according to a protocol supported by the target network and computing device. Examples of possible protocols include HTTP, TCP/IP, WAP, Bluetooth, etc.

At block 1012, the system 208 delivers the content to the notification receiver's computing device, where it is presented for review by the notification receiver.

CONCLUSION

Although the invention has been described in language specific to structural features and/or methodological steps, it is to be understood that the invention defined in the appended claims is not necessarily limited to the specific features or steps described. Rather, the specific features and steps are disclosed as preferred forms of implementing the invention.

What is claimed is:

1. A system comprising:
an implantable cardiac therapy device (ICTD);
a computing network configured to communicate with notification devices; and
a notification architecture implemented by the computing network to distribute a notification message to a user of the ICTD through the notification devices and according to different formats and protocols supported by the notification devices;
wherein the notification architecture comprises:
a processing layer to process the data received from the ICTD and generate a notification message based, at least in part, upon such data; and
a notification layer, separate from the processing layer, to format and encode a notification message according to the formats and protocols supported by the notification devices; and
wherein the computing network is configured to distribute the notification messages to notification devices selected from a group of notification devices comprising a computer, a portable computer, a personal digital assistant, a wireless phone, landline telephone, a pager, a facsimile, and a database.

2. A system as recited in claim 1, wherein the notification architecture comprises:
one or more records that specify the notification devices used by the user of the ICTD; and
a specification store to maintain user interface definitions and style sheets specifying how the data should be presented on a particular notification device.

3. A system as recited in claim 1, wherein the notification architecture comprises:
a content formatter to format the data in different formats for notification on the notification devices;
a protocol encoder to encode the data according to different protocols supported by the notification devices.

4. A system as recited in claim 1, wherein the implantable cardiac therapy device comprises a cardiac stimulation device.

5. A system as recited in claim 1, wherein the notification architecture is further implemented by the computing network to distribute a notification message to one or more of the following associated with the user of the ICTD: a healthcare provider, a pharmacist, a physician, a caregiver, through the notification devices and according to different formats and protocols supported by the notification devices.

6. A system as recited in claim 1, wherein the specific format and protocol employed by the notification devices may be selected from a group consisting of e-mail, voice mail, pager, fax, WAP, and SMS.

7. A notification architecture for distributing notification messages related to implantable cardiac therapy devices (ICTDs) to various notification devices of ICTD users, the notification architecture comprising:
   an information source layer configured to collect the data from the ICTD;
   a processing layer configured to process the data received from the ICTD and generate a notification message based, at least in part, upon such data;
   a notification layer, separate from the processing layer, configured to format and encode a notification message according to the formats and protocols supported by a receiving notification device;
   wherein the various notification devices comprises a computer, a portable computer, a personal digital assistant, a wireless phone, landline telephone, a pager, a facsimile, and a database.

8. A notification architecture as recited in claim 7, wherein the notification layer comprises:
   one or more records that specify the notification device used by the user of the ICTD;
   a specification store to maintain user interface definitions and style sheets specifying how the data should be presented on a particular notification device.

9. A notification architecture as recited in claim 7, wherein the notification layer comprises:
   a content formatter to format the data in different formats for notification on the notification devices;
   a protocol encoder to encode the data according to different protocols supported by the notification devices.

* * * * *